United States Patent [19]

Vladuchick

[11] 4,346,219

[45] Aug. 24, 1982

[54] PROCESS FOR PREPARING DESACETOXYCEPHALOSPORANIC ACID

[75] Inventor: William C. Vladuchick, Indianapolis, Ind.

[73] Assignee: Eli Lilly and Company, Indianapolis, Ind.

[21] Appl. No.: 278,780

[22] Filed: Jun. 29, 1981

[51] Int. Cl.³ .......................................... C07D 501/04
[52] U.S. Cl. ........................................ 544/28; 544/30
[58] Field of Search .................................... 544/28, 30

[56] References Cited

U.S. PATENT DOCUMENTS

| | | | |
|---|---|---|---|
| 3,134,774 | 5/1964 | Chow et al. | 544/30 |
| 3,773,761 | 11/1973 | Blackburn et al. | 544/30 |
| 3,929,775 | 12/1975 | Ochiai et al. | 544/30 |
| 3,991,051 | 11/1976 | Breuer et al. | 544/30 |
| 4,051,131 | 9/1977 | Robinson | 544/28 |

OTHER PUBLICATIONS

Aries, *Chemical Abstracts*, 84P121874f (1976).

*Primary Examiner*—Paul M. Coughlan, Jr.
*Attorney, Agent, or Firm*—William B. Scanlon; Arthur R. Whale

[57] ABSTRACT

Process for preparing 7-ADCA and 7-(N,N-disubstituted)aminodesacetoxycephalosporins which comprises reacting 7-ACA or an N,N-disubstituted derivative thereof with a tri-($C_1$–$C_6$ alkyl)silane in a highly acidic organic acid, e.g. trifluoroacetic acid, with a Lewis acid, preferably boron trifluoride, at a temperature of 20° C. to 100° C. E.g., 7-ADCA is readily prepared in high yield, is purified by isoelectric precipitation, and is useful for preparing cephalexin.

10 Claims, No Drawings

PROCESS FOR PREPARING DESACETOXYCEPHALOSPORANIC ACID

BACKGROUND OF THE INVENTION

This invention relates to a process for the preparation of cephalosporin compounds. In particular, it relates to a process for the preparation of 7-(N,N-disubstituted)-3-methyl-3-cephem compounds and 7-aminodesacetoxycephalosporanic acid hereinafter referred to by the commonly used abbreviation 7-ADCA. 7-ADCA is useful as an intermediate for the preparation of desacetoxycephalosporin antibiotic compounds, in particular, cephalexin. The N,N-disubstituted desacetoxycephalosporins can be converted to 7-ADCA.

7-ADCA has been obtained by the hydrogenolysis of the cephalosporin C nucleus 7-aminocephalosporanic acid (7-ACA), Stedman, et al., *J. Med. Chem.* 7, 117 (1964); U.S. Pat. No. 3,124,576.

SUMMARY OF THE INVENTION

7-Amino- and 7-(N,N-disubstituted)aminocephalosporanic acids are converted to the corresponding 3-methyl-3-cephem-4-carboxylic acids by reacting the cephalosporanic acid with a tri($C_1$–$C_6$ alkyl)silane in the presence of an organic acid having a pKa of <1.5 and a Lewis acid. For example, 7-aminocephalosporanic acid (7-ACA) is reacted with triethylsilane in trifluoroacetic acid in the presence of boron trifluoride to provide 7-aminodesacetoxycephalosporanic acid (7-ADCA).

Examples of 7-(N,N-disubstituted)aminocephalosporanic acids are the N,N-disilylated derivatives of 7-ACA such as 7-(bis-trimethylsilylamino)cephalosporanic acid, and the 7-diacylated derivatives of 7-ACA such as 7-phthalimidocephalosporanic acid and 7-succinimidocephalosporanic acid.

The 7-(N,N-disubstituted)aminodesacetoxycephalosporanic acids provided by the process are generally useful as intermediates. In particular, the N,N-disilylated derivatives are hydrolyzed to 7-ADCA. 7-ADCA is a valuable intermediate useful in the preparation of cephalosporin antibiotics, in particular, the well-known orally effective antibiotic cephalexin.

DETAILD DESCRIPTION OF THE INVENTION

According to the process of this invention, a cephalosporanic acid represented by the formula 1

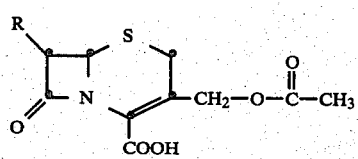

is reacted with a tri($C_1$–$C_6$ alkyl)silane in a reaction medium containing an organic acid having a pKa of <1.5 and a Lewis acid to provide a desacetoxycephalosporanic acid represented by the formula 2

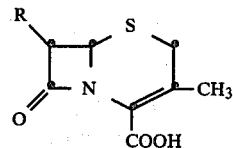

where in formulas 1 and 2, R is an amino group or a disubstituted amino group. The process is illustrated by the following reaction scheme

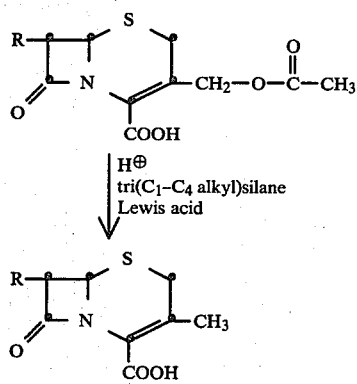

Examples of trialkylsilanes which can be employed in the process include trimethylsilane, triethylsilane, tri-n-propylsilane, tri-n-butylsilane, tri-n-pentylsilane, tri-n-hexylsilane, and the corresponding branched trialkylsilanes. A preferred trialkylsilane of this invention is triethylsilane.

The reaction is carried out under substantially anhydrous conditions in the presence of the strong organic acid and a Lewis acid. Examples of the highly acidic organic acids which can be used in the process are the halogenated acetic acids such as trifluoroacetic acid, trichloroacetic acid, tribromoacetic acid, and the like; and the alkyl and halogenated alkyl sulfonic acids such as methanesulfonic acid, ethanesulfonic acid, trichloromethanesulfonic acid, fluoromethanesulfonic acid, and the like. A preferred strong organic acid of this invention is trifluoroacetic acid.

Examples of Lewis acids which can be employed in the process are those recognized as potent Lewis acids such as boron trifluoride, boron trichloride, aluminum trichloride, stannic chloride, titanium tetrachloride, zinc chloride, ferric bromide, trimethylboron, and like Lewis acids. The preferred Lewis acid of this invention is boron trifluoride which can be used in the commonly available etherate form.

An inert organic solvent can be employed in the process; however, certain of the strong organic acids used in the process can be conveniently used as the solvent. Inert organic solvents such as the halogenated hydrocarbon solvents, for example, methylene chloride, chloroform, dichloroethane, and the like can be used.

The reaction can be carried out at a temperature between about 20° C. and about 100° C. and preferably at a temperature between about 35° C. and 70° C. The reaction involved in the process is exothermic. The initation of the reaction and the extent to which the temperature increases are dependent on such factors as the concentration of the reaction mixture, whether a solvent is employed, the starting material, and other factors. Compounds of the formula 1 wherein R is a disubstituted amino group, e.g. phthalimido, afford better yields of the 3-methyl product at temperatures of about 25° C. to about 55° C., while when R is amino (7-ACA) better yields of the 7-ADCA product are obtained at temperatures between about 45° C. and about 75° C.

In carrying out the process, the strongly acidic organic acid is used in excess to insure high acidity in the reaction medium. The trialkylsilane is employed in amounts corresponding to between about 2 and about 4 moles per mole of the cephalosporanic acid employed. The Lewis acid can be employed in excess; however, in general, between 2.5 and 4 moles of Lewis acid per mole of cephalosporanic acid is employed. The process is carried out as follows. The cephalosporanic acid (formula 1) is mixed with the excess organic acid and the trialkylsilane is added to the mixture. With stirring at about room temperature or slightly above, the Lewis acid is added. Upon the addition of the Lewis acid, an exothermic reaction occurs and is allowed to proceed without cooling. However, in carrying out the process of this invention on a large manufacturing scale, the temperature should be controlled to prevent the development of degradation products in the reaction. In most instances, however, on small to medium-size scale reactions, the temperature is allowed to rise and external cooling is not required. After the reaction has subsided, the mixture is stirred for between about 4 and about 6 hours to insure completion of the reaction.

A solvent is employed in the reaction when the highly acidic organic acid is not suitable as a solvent. Solvents such as methylene chloride and trichloroethane are suitably used in the process with such acids. The solvent is preferably dried before use. For large scale manufacturing a solvent can be used to moderate the reaction.

Examples of 7-(N,N-disubstituted)aminocephalosporanic acids, represented by the formula 1, which can be used in the process are the 7-diacylated derivatives represented by the formula

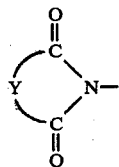

wherein Y is phenylene, $C_1$–$C_3$ alkylene, or $C_2$–$C_3$ alkenylene. Examples of such diacyl groups are phthalimido, succinimido, glutarimido, maleimido, and the like.

The N,N-disubstituted amino group represented by R in the formula 1 also includes a disilylated amino group represented by the formula

[($C_1$–$C_4$ alkyl)$_3$Si]$_2$—N— or a cyclic disilylated amino group of the formula

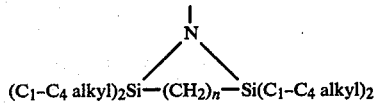

In the above formulas "alkyl" refers to the $C_1$–$C_4$ hydrocarbon groups such as methyl, ethyl, n-propyl, n-butyl, iso-butyl, iso-propyl, and the like. In the formula representing the cyclic disilylated amino group "n" is 2 or 3.

Examples of such disilylated amino groups are bis(trimethylsilyl)amino, bis(triethylsilyl)amino, bis(tri-n-butylsilyl)amino, and cyclic disilylated amino groups represented by the formulas

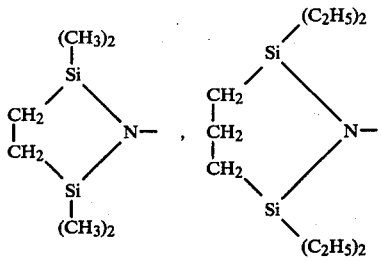

The compounds of the formula 1 wherein R is a disubstituted amino group are prepared by methods known in the art. For example, the disilylated derivatives of 7-ACA are prepared by reacting 7-ACA under anhydrous conditions with a trialkyl chlorosilane such as trimethylchlorosilane, triethylchlorosilane, tri-n-butylchlorosilane, 1,2-ethylene-bisdimethylchlorosilane, and the like.

Examples of the 7-(N,N-disubstituted amino)-desacetoxycephalosporins obtained by the process and represented by the formula 2 are 7-phthalimidodesacetoxycephalosporanic acid, 7-succinimidodesacetoxycephalosporanic acid, 7-maleimidodesacetoxycephalosporanic acid, 7-[di-(trimethylsilyl)amino]desacetoxycephalosporanic acid, and 7-[di-(triethylsilyl)amino]desacetoxy cephalosporanic acid.

It will be readily appreciated by those in the art that when the process is carried out with a disilylated 7-ACA derivative that the $C_4$ carboxylic acid function of 7-ACA can likewise be silylated as a silyl ester.

The disilylated products of the process are useful intermediates which undergo acidic hydrolysis to 7-ADCA. The N,N-diacylated derivatives of 7-ACA likewise are useful intermediates to 7-ADCA which on N-deacylation afford 7-ADCA. For example, 7-phthalimido-3-methyl-3-cephem-4-carboxylic acid is N-deacylated with hydrazine. These N,N-diacylated products also possess antibacterial properties which render the compounds useful as antiseptics, topical sterilants, and decontaminants.

The process of this invention is particularly useful for the direct conversion of 7-ACA to 7-ADCA (formulas 1 and 2, R=NH$_2$).

The process affords 7-ADCA in the form of the salt formed with the organic acid used in the process. 7-ADCA can be isolated in the salt form or preferably it can be isolated in the zwitterionic form as follows. In the instance where the process is carried out by using the organic acid as the solvent, the reaction mixture is diluted with a non-polar organic solvent to precipitate the 7-ADCA salt. The salt is separated from the aqueous phase and is dissolved in an aqueous solvent such as a mixture of water and dimethylformamide. The pH of the solution is adjusted to the isoelectric point of 7-ADCA (ca 4.0) and the precipitate of 7-ADCA in the zwitterionic form is separated.

In the instance where a chlorinated hydrocarbon solvent is used in the process, the salt form of 7-ADCA commonly precipitates. The salt is separated and 7-ADCA zwitterion is obtained from an aqueous solution of the salt by isoelectric precipitation. When in such instance the 7-ADCA salt is at least partially soluble in the reaction mixture, the mixture is evaporated and the salt dissolved in an aqueous solvent for isoelectric precipitation of 7-ADCA.

In a preferred embodiment of the process of this invention, 7-aminocephalosporanic acid is dissolved in excess trifluoroacetic acid and triethylsilane is added to the mixture with stirring. Next, boron trifluoride etherate is added with stirring and the exothermic reaction is allowed to proceed without external cooling. The reaction mixture is stirred while cooling and thereafter is diluted with a relatively non-polar organic solvent such as diethyl ether to precipitate the product, 7-ADCA as the trifluoroacetate salt. In order to separate the trifluoroacetate salt from impurities, the salt is dissolved in an aqueous organic solvent mixture such as water and dimethylformamide. The solution is filtered to remove any insoluble matter. The aqueous filtrate can be further diluted with water, if necessary, and the pH of the filtrate is adjusted to the isoelectric point of 7-aminodesacetoxycephalosporanic acid. The 7-ADCA precipitates in the intramolecular salt form, the zwitterionic form, and is separated by filtration, centrifugation, or other suitable means. The 7-ADCA can be washed with an organic solvent such as acetone to remove traces of water and acidic materials carried over from the precipitation. 7-Aminodesacetoxycephalosporanic acid can be further purified, if desired, by standard recrystallization procedures known in the art.

The above process is illustrated by the following reaction scheme.

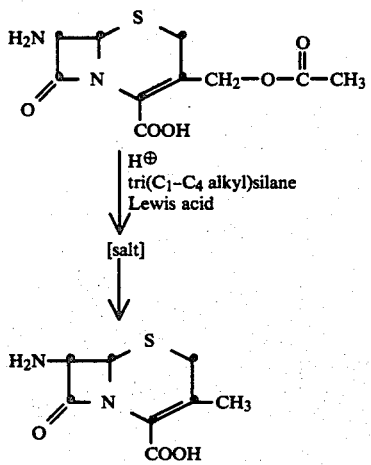

The process described herein is adaptable to continuous processing particularly the preferred embodiment providing 7-ADCA.

7-ADCA is useful for preparing desacetoxycephalosporanic acid antibiotics. For example, 7-ADCA can be acylated with the desired carboxylic acid to obtain such antibiotics. Cephalexin is obtained with 7-ADCA by the procedures described by Ryan, et. al., *J. Med. Chem.* 12, 310 (1969).

The process of this invention is further illustrated by the following examples.

EXAMPLE 1

To a solution of 2.26 g. (8.3 mmole) of 7-ACA in about 15 ml. of trifluoroacetic acid were added at room temperature with stirring 5 ml. of triethylsilane followed by 8-9 ml. of boron trifluoride etherate. The reaction mixture was heated to above 60° C. (exothermic). After the reaction mixture was cooled to room temperature and diluted with diethyl ether, the precipitate of 7-ADCA trifluoroacetate salt was filtered and air dried. The product was dissolved in water and the pH of the solution was adjusted to 4.04 to precipitate 7-ADCA zwitterion. The product was dried. The weight of dried product (tannish powder) was 1.47 g. (83% yield).

EXAMPLE 2

To a 250 ml. 3-necked round bottom flask equipped with a thermometer, stirrer, condenser and dropping funnel were added 10.88 g. (40 mmole) of 7-aminocephalosporanic acid and 70.5 ml. of trifluoroacetic acid. Triethylsilane (17.2 g., 150 mmole, 23.6 ml.) was added to the solution followed by 33.6 ml. of methylene chloride. The resulting solution was stirred at room temperature and 27.1 g. (190.7 mmole, 23.6 ml.) of boron trifluoride etherate were added. The temperature of the reaction mixture rose to about 55° C. following the addition of the boron trifluoride. After the temperature of the mixture had cooled to room temperature, the mixture was poured with stirring into 250 ml. of diethyl ether. The precipitate of the trifluoroacetate salt of 7-aminodesacetoxycephalosporanic acid was separated by filtration and was dissolved in 100 ml. of water containing 50 ml. of acetone. The pH of the orange-colored solution was adjusted to 4.0 with ammonium hydroxide to precipitate 7-ADCA in the zwitterionic form. The product was separated by filtration and was washed with aqueous acetone, acetone, and then with diethyl ether and was dried. There were obtained 7.23 g. (84.5% yield) of 7-ADCA as a fine off-white powder.

EXAMPLE 3

7-Phthalimido-3-methyl-3-cephem-4-carboxylic acid

A solution of 0.775 g. (1.92 mmole) of 7-phthalimidocephalosporanic acid, 0.88 g. (6.3 mmole) of triethylsilane, and 3.2 ml. of trifluoroacetic acid in 3 ml. of methylene chloride was cooled to 5° C. in an ice-bath and 0.86 g. (6 mmole) of boron trifluoride etherate were added via syringe. The reaction mixture was stirred at 5° C. for 15 minutes, the cooling bath was removed, and stirring continued for one hour until the reaction was completed as shown by thin layer chromatography (silica gel; 7:4:1, ethyl acetate:toluene:acetic acid, v:v:v). The reaction mixture was poured into 150 ml. of ethyl acetate and the solution was washed with water, aqueous 1 N hydrochloric acid, and with brine. The solution was dried over sodium sulfate and then evaporated in vacuo to yield 0.53 g. (80% yield) of the product as a light tan foam. The nmr spectrum and mass spectrum of the product were in agreement with the structure of the title compound.

EXAMPLE 4

The preparation of 7-phthalimido-3-methyl-3-cephem-4-carboxylic acid described by Example 3 was repeated without controlling the internal temperature during the addition of the boron trifluoride etherate. An exotherm carried the temperature from room temperature to 35° C. The yield and purity of the product obtained were comparable to that obtained in Example 3.

EXAMPLE 5

7-ADCA via 7-[di-(trimethylsilyl)amino]cephalosporanic acid

To a solution of 7-[di-(trimethylsilyl)amino]cephalosporanic acid in dry methylene chloride containing trifluoroacetic acid and triethylsilane is added boron trifluoride etherate, and the solution is stirred without cooling for about 2 hours. The reaction mixture is diluted with water and is stirred for about 15 minutes to effect the hydrolysis of the trimethylsilyl groups. The mixture is then poured into diethyl ether to precipitate the 7-ADCA trifluoroacetate salt. The salt can then be converted to 7-ADCA in zwitterionic form by the procedure described by Example 1.

I claim:

1. A process for preparing a desacetoxycephalosporanic acid of the formula

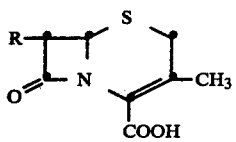

which comprises mixing at a temperature between about 20° C. and about 100° C. a cephalosporanic acid of the formula

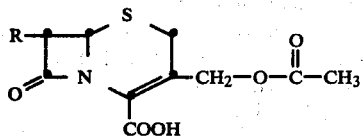

with a tri($C_1$-$C_6$ alkyl)silane in the presence of an organic acid having a pKa of less than 1.5 and a Lewis acid; wherein R is amino or disubstituted amino.

2. The process of claim 1 wherein R is disubstituted amino.

3. The process of claim 2 wherein the disubstituted amino group is a diacylated amino group of the formula

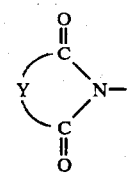

wherein Y is phenylene, $C_1$-$C_3$ alkylene, or $C_2$-$C_3$ alkenylene.

4. The process of claim 3 wherein R is phthalimido, the Lewis acid is boron trifluoride, and the organic acid is trifluoroacetic acid.

5. The process of claim 2 wherein R is a disilylated amino group of the formula

[($C_1$-$C_4$ alkyl)$_3$Si]$_2$—N— or a cyclic disilylated amino group of the formula

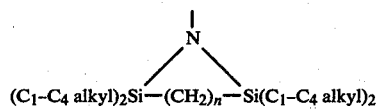

wherein n is 2–4.

6. The process of claim 1 wherein R is amino.

7. The process of claim 6 wherein the Lewis acid is selected from the group consisting of boron trifluoride, boron trichloride, aluminum trichloride, stannic chloride, titanium tetrachloride, zinc chloride, ferric bromide, and trimethyl boron.

8. The process of claim 6 wherein the organic acid is selected from the group consisting of trifluoroacetic acid, trichloroacetic acid, tribromoacetic acid, and fluoromethanesulfonic acid.

9. The process of claim 6 wherein triethylsilane, trifluoroacetic acid and boron trifluoride are mixed with 7-aminocephalosporanic acid.

10. The process of claim 9 wherein a halogenated hydrocarbon is used as an inert solvent.

* * * * *